(12) United States Patent
Molin et al.

(10) Patent No.: US 7,947,482 B2
(45) Date of Patent: May 24, 2011

(54) STRAINS OF BIFIDOBACTERIUM HAVING THE ABILITY TO PRODUCE GLUTAMINE

(75) Inventors: Goran Molin, Bjarred (SE); Siv Ahrne, Bjarred (SE); Bengt Jeppsson, Lund (SE)

(73) Assignee: Probi AB, Lund (SE)

( * ) Notice: Subject to any disclaimer, the term of this patent is extended or adjusted under 35 U.S.C. 154(b) by 894 days.

(21) Appl. No.: 10/543,604

(22) PCT Filed: Jan. 27, 2004

(86) PCT No.: PCT/SE2004/000098
§ 371 (c)(1),
(2), (4) Date: Jun. 30, 2006

(87) PCT Pub. No.: WO2004/067731
PCT Pub. Date: Aug. 12, 2004

(65) Prior Publication Data
US 2006/0269533 A1 Nov. 30, 2006

Related U.S. Application Data

(60) Provisional application No. 60/447,274, filed on Feb. 14, 2003.

(30) Foreign Application Priority Data

Jan. 31, 2003 (SE) ...................................... 0300245

(51) Int. Cl.
*C12N 1/20* (2006.01)
(52) U.S. Cl. .................................... 435/252.1; 424/93.4
(58) Field of Classification Search .................. None
See application file for complete search history.

(56) References Cited

U.S. PATENT DOCUMENTS

| | | | |
|---|---|---|---|
| 5,462,924 | A | 10/1995 | Kihlberg et al. |
| 6,077,504 | A | 6/2000 | Cavaliere Ved. Vesley et al. |
| 6,203,797 | B1 | 3/2001 | Perry |
| 6,468,525 | B1 | 10/2002 | Watson et al. |
| 2002/0006432 | A1 | 1/2002 | Collins et al. |

FOREIGN PATENT DOCUMENTS

| | | |
|---|---|---|
| EP | 0 555 618 | 8/1993 |
| JP | 59 155321 | 9/1984 |
| WO | 01/83700 | 11/2001 |
| WO | WO 02/3879 | * 5/2002 |
| WO | WO 02/060276 A1 | 8/2002 |
| WO | WO 02/062360 A1 | 8/2002 |

OTHER PUBLICATIONS

Yano et al., Biosci Microflora, vol. 18;No. 1;p. 31-36(1999).*
Hatanaka et al., Agricultural and biological chemistry, 1987, vol. 51, pp. 251-252.*
Hoyos, International Journal of Infectious Diseases, vol. 3, Issue 4, Summer 1999, pp. 197-202.*
Yano, Toshihiro et al. "Selective growth and mechanism of related enzymes of bifidobacteria", Rakuno Kagaku, Shokuhin no Kenkyu, vol. 39, No. 6, pp. A229-A237, CAPLUS accession No. 1991:554686, English abstract only 1991.
Anderson, Peter et al. "Oral Glutamine Reduces the Duration and Severity of Stomatitis after Cytotoxic Cancer Chemotherapy", Cancer, vol. 83, pp. 1433-1439 1998.
Houdijk, Alexander PJ et al. "Randomised trial of glutamine-enriched enteral nutrition on infectious morbidity in patients with multiple trauma", The Lancet, vol. 352, pp. 772-776 1998.
Matteuzzi, D. et al. "Amino Acids Produced by Bifidobacteria and Some Clostridia", Ann. Microbiol., vol. 129B, pp. 175-181 1978.
Hatanaka, Masayuki et al. "Distribution and Some Properties of Glutamine Synthetase and Glutamate Dehydrogenase in Bifidobacteria", Agric. Biol. Chem., vol. 51, No. 1, pp. 251-252 1987.
Masayuki Hatanaka, et al., "Purification and Some Properties of Glutamine Synthetases from Bifidobacteria", Agric. Biol. Chem., vol. 51, No. 2, 1987, pp. 425-433.
A. Shihata, et al., "Proteolytic Profiles of Yogurt and Probiotic Bacteria", International Dairy Journal, vol. 10, 2000, pp. 401-408.

* cited by examiner

*Primary Examiner* — Irene Marx
(74) *Attorney, Agent, or Firm* — Oblon, Spivak, McClelland, Maier & Neustadt, L.L.P.

(57) ABSTRACT

The invention refers to new strains of *Bifidobacterium*, especially of the species *Bifidobacterium infantis*, having the ability to survive in the intestinal tract and to produce glutamine and optionally arginine in vivo, as well as to compositions comprising said strains.

3 Claims, 6 Drawing Sheets

STRAINS OF BIFIDOBACTERIUM HAVING THE ABILITY TO PRODUCE GLUTAMINE

FIELD OF THE INVENTION

The present invention refers to new strains of *Bifidobacterium* having the ability to produce glutamine and optionally arginine in vivo.

BACKGROUND OF THE INVENTION

Glutamine is the most abundant amino acid in the body. It is a "nitrogen shuttle" between tissues and a fuel for enterocytes, colonocytes, lymphocytes and proliferating cells. The function of the gut is impaired in patients with glutamine deficiency, particularly because of the loss of protection against the translocation of bacteria and/or endotoxin from the gut lumen into the portal circulation. Glutamine depletion occurs in critically ill and injured patients, and may contribute to the high rate of infection and muscle depletion.

Enteral administration of glutamine has conferred health beneficial effects in patients with different indications. In intensive care unit patients with multiple organ dysfunction administration of glutamine decreased infectious complications in the patients (Houdijk et al., Lancet, 352:772-776, 1998). Similar effects were observed in patients undergoing bone marrow transplantation receiving glutamine supplemented parenteral nutrition (Ziegler et al., Annals Internal Medicine, 116:821-828, 1992). Another example is patients with short bowel syndrome, which had a substantial improvement of their absorption capacity following glutamine supplementation (Byrne et al., Annals of Surgery, 222:243-255, 1995). Oral glutamine supplementation during and after chemotherapy has also been shown to significantly reduce both the duration and the severity of chemotherapy-associated stomatitis. It was concluded that oral glutamine appeared to be a simple and useful measure to increase the comfort of many patients at high risk of developing mouth sores as a consequence of intensive cancer chemotherapy (Anderson et al., Cancer 1998; 83:1433-9). Nutritional supplementation of glutamine after intensive exercise has also decreased the incidence of infections, particularly of upper respiratory tract infections (Castell, *Amino acids* 2001; 20(1):49-61). However, the precise effect of glutamine on immunodepression has not yet been established.

A major technical difficulty with glutamine is that during processing and storage glutamine is easily converted to glutamic acid (glutamate), i.e. glutamine is a relatively unstable compound that is difficult to incorporate into formulas intended for oral administration. Furthermore, the orally administered glutamine will in the sour environment of the stomach to a high degree be converted into glutamic acid and never reach the intestine and be absorbed as glutamine.

Arginine enhances the immune function and promotes wound healing. Administration of arginine has been used in postoperative patients and patients under intensive care. In most clinical studies arginine has been administered together with other substances such as RNA and fish oil. There are indications that administration of arginine modulates postoperative immune response. Daly, John E., et al., *Surgery* 112:55-67, 1992 show that enteral nutrition with supplemental arginine, RNA and omega-3-fatty acids in patients after operation improves the immune defence through different mechanisms. Arginine reduces complications in patients undergoing chemoradiation and surgery (Tepaske et al., 2001; *Lancet* 358: 696-701), and reduces length of stay for intensive care unit patients (Bauer et al., 1995, *Critical Case Medicine* 23: 436-449).

An increased survival could be observed in animals fed with an arginine-supplemented diet. Quantitative colony counts and the calculated percentage of remaining viable bacteria showed that the ability to kill translocated organisms was signify-cantly enhanced in animals receiving arginine (Adawi, D., et al., 1997, Hepatology 25: 642-647).

Strains of *Bifidobacterium* spp., that is bifidobacteria, are often present in high numbers in the human colon, especially in breast fed babies. Bacteria from the *Bifidobacterium* spp. are regarded as probiotics, that is live bacteria that upon ingestion provide health beneficial effects to the host. High numbers of *Bifidobacterium* spp. in colon have been claimed to have health beneficial effects. However, the course of action of said beneficial effects is largely unknown.

PRIOR ART

Matteuzzi et al. [*Ann. Microbiol.* (*Inst. Pasteur*) 1978; 129 B, 175-181] investigated a large number of bifido-bacteria from different habitats for their capacity to release free amino acids in culture broths. The data obtained indicated that several species of bifidobacteria were capable of synthesising all the amino acid needed for growth and also to liberate said compounds into the culture broths. *B. thermophilum, B. bifidum* and *B. adolescentis* were found to be the best producers, and the amino acids most commonly found in the culture broths were mainly alanine, valine, and aspartic acid. It was speculated that *Bifidobacterium* spp. play a role in the amino acid metabolism of the gastrointestinal tract.

WO 01/83700 (University of Maryland) discloses a composition and method for treating and preventing gastro-intestinal injury, neonatal necrotising enterocolitis (NEC) and bacterial sepsis. The composition includes a combination of Gram (+) bacteria, in particular *Lactobacillus* and *Bifidobacterium*, and glutamine, and should be orally or naso-orally administrated. The composition is said to block translocation of bacterial agents such as Gram (−) bacteria.

Glutamine administered intravenously is very efficient but expensive and complicated. A better way to administer glutamine would of course be to use a bacterial strain having the ability to produce substantial amounts of glutamine in the intestines. Until now, however, no such strains have been described.

SUMMARY OF THE INVENTION

It has now surprisingly been found that specific strains of *Bifidobacterium* are capable of producing glutamine in a growth medium mimicking the environment in the human colon. Said strains can thus be used for producing glutamine in vivo after oral or enteral administration to a mammal, especially a human. Some of the strains are also capable of producing arginine.

DESCRIPTION OF THE INVENTION

The invention refers to a strain of *Bifidobacterium* having the ability to survive in the intestinal tract and to produce glutamine in vivo. Especially glutamine is produced in the human colon. Survive in this context means that the bacterial strains have been isolated on different sampling occasions in faeces from an individual. Thus, the bacteria obviously grow and survive in their host for a while. The bifidobacterial strains of the invention can grow on nutrient media having a pH below 7, especially 5.5-6.5. Rogosa agar is one example of such a medium, another is MRS.

According to a preferred aspect the new strains also have the ability to assimilate ammonia.

The invention especially refers to strains belonging to the species *Bifidobacterium infantis*.

According to a specific aspect the invention also refers to a strain of *Bifidobacterium* which has the 16S rRNA genes located on single DNA fragments with molecular sizes of about 2840 kb, obtained by cleaving chromosomal DNA with Hind III, followed by separation of fragments by agarose gel electrophoresis, and by hybridisation with a DIG-labelled 420 bp fragment probe (position 506 to 926, *E. coli* numbering) of the 16S rRNA gene of *L. casei* subsp. *pseudoplantarum* DSM 20008 using Southern blot hybridisation. Such strains are, for example, the strains, deposited at the Deutsche Sammlung von Mikroorganismen und Zellkulturen GmbH (Mascheroder Weg 1b, D-38124 Braunschweig) on Aug. 23, 2002, *Bifidobacterium infantis* CURE 19 (DSM 15158); *Bifidobacterium infantis* CURE 21 (DSM 15159); *Bifidobacterium infantis* CURE 26 (DSM 15160); *Bifidobacterium infantis* CURE 28 (DSM 15161); *Bifidobacterium infantis* CURE 29 (DSM 15162).

According to another aspect the invention also refers to a strain of *Bifidobacterium* which has the 16S rRNA genes located on single DNA fragments with molecular sizes of about 895 kb, obtained by cleaving chromosomal DNA with EcoRI, followed by separation of fragments by agarose gel electro-phoresis, and by hybridisation with a DIG-labelled 420 bp fragment probe (position 506 to 926, *E. coli* numbering) of the 16S rRNA gene of *L. casei* subsp. *pseudoplantarum* DSM 20008 using Southern blot hybridisation. According to a preferred aspect said strain is able to produce glutamine without reducing glutamic acid.

The invention especially refers to the strains *Bifidobacterium infantis* CURE 21 and *Bifidobacterium infantis* CURE 26, which were deposited at the Deutsche Sammlung von Mikroorganismen und Zellkulturen GmbH on Aug. 23, 2002 and were given the accession numbers DSM 15159 and DSM 15160, respectively, or variants thereof. Said strains are able to produce glutamine without reducing glutamic acid.

According to another aspect the invention also refers to a strain of *Bifidobacterium* which has the 16S rRNA genes located on single DNA fragments with molecular sizes of about 3420 kb, obtained by cleaving chromosomal DNA with EcoRI, followed by separation of fragments by agarose gel electro-phoresis, and by hybridisation with a DIG-labelled 420 bp fragment probe (position 506 to 926, *E. coli* numbering) of the 16S rRNA gene of *L. casei* subsp. *pseudoplantarum* DSM 20008 using Southern blot hybridisation. According to a preferred aspect said strain has the ability to produce arginine.

The invention also especially refers to the following strains, which have all been deposited at the Deutsche Sammlung von Mikroorganismen und Zellkulturen GmbH on Aug. 23, 2002, and been given a deposition number, that is *Bifidobacterium infantis* CURE 19, DSM 15158, *Bifidobacterium infantis* CURE 28, DSM 15161, and *Bifidobacterium infantis* CURE 29, DSM 15162, and to variants thereof. Said strains are able to produce in addition to glutamine also arginine.

The new strains have all been isolated from faeces from young children and selected by culturing on agar at a pH below 7. The strains have subsequently been characterised by ribotyping and REA.

Another object of the invention is a composition comprising one or more strains of *Bifidobacterium* of the invention in combination with a carrier. Examples of carriers are oatmeal gruel, lactic acid fermented foods, inulin, lactulose, fructo-oligosaccharides, resistent starch, β-glucans and guar gum. In order to improve the proliferation of the bifidobacteria and increase the production of glutamin and arginine, respectively, and enhance the ammonia assimilation in colon dietary fibres should be added to the composition. Dietary fibres are for instance inulin, fructo-oligo-saccharides, maltodextrins, β-glucans and guar gum. The invention thus also refers to a composition as described comprising in addition dietary fibres.

The compositions of the invention, such as suspensions, tablets, capsulas, powders, can be administrated orally. They can also be administrated as an enema.

The composition of the invention can be a food composition wherein the carrier is a food product. The glutamine producing *Bifidobacterium*-strains can be given to young children, elderly people, athletics and ordinary consumers that wish to keep-fit to improve muscle function and avoid immune depression following exercise. The arginine producing *Bifidobacterium*-strains can be given to ordinary consumers that want to keep-fit and avoid negative influence on immune function.

The composition of the invention can be a pharmaceutical composition, wherein the carrier is a therapeutically acceptable carrier. The glutamine producing strains, as well as the arginine producing strains can in addition be used in formulas for enteral feeding.

The ammonia assimilating *Bifidobacterium* strains of the invention can be given to patients with temporary kidney failure such as seen in patients under intensive care following surgery and complications or following other diseases, such as severe infections, intoxications. In such cases the kidney function can be expected to return and a treatment aimed at reducing the nitrogen load from the gut may avoid the need for dialysis. The ammonia assimilating strains can be administered to patients with liver failure and encephalopathy, e.g. in hepatitis or intoxication or following alcohol abuse. A reduced absorption of nitrogenous substances from the gut will in those situations improve encephalopathy and liver function. The ammonia assimilating *Bifidobacterium* strains can be given to young children, elderly people or consumers with underlying diseases that hamper their liver capacity for the conversion of ammonia to urea or having an increased absorption of nitrogen from the gut, e.g. patients with chronic renal or liver failure of small to moderate degree not yet in need of transplantation or dialysis.

According to a special aspect the composition of the invention can also comprise one or more *Lactobacillus* strains.

In addition to the optional beneficial effects of the lactobacilli per se, said bacteria can protect the bifidobacteria from the harmful influence of oxygen.

According to another aspect, the invention refers to one or more strains belonging to the species *Bifidobacterium infantis* for use in therapy.

The invention refers to the use of one or more of the strains *Bifidobacterium infantis* CURE 19, DSM 15158; *Bifidobacterium infantis* CURE 21, DSM 15159; *Bifidobacterium infantis* CURE 26, DSM 15160; *Bifidobacterium infantis* CURE 28, DSM 15161; *Bifidobacterium infantis* CURE 29, DSM 15162; or a variant thereof for the preparation of a medicament for treatment of intensive care patients with multiple organ dysfunction and intestinal failure, for prophylaxis in chemotherapy patients and patients with inflammatory diseases and postoperative administration after major surgery.

EXPERIMENTAL

Isolation of Strains

All strains were isolated from faeces of young children, age one week to one year. The faeces samples were serial diluted in a dilution solution (0.9% [w/v] NaCl, 0.1% [w/v] peptone, 0.1% [w/v] Tween 80, 0.02% [w/v] cystein-HCl) and spread on Rogosa agar plates. Isolates were selected with respect to their ability to grow on Rogosa agar, pH 5.4, and repeated isolation from one individual. The isolates were picked from the Rogosa agar plates after incubation at 37° C. for 72 hours. They were identified to genus level by genus specific PCR (Roy et al., 2000; *FEMS Microbiological Letters* 191:17-24) and to species level by 16S rDNA sequencing (Pettersson et al., 2002; *Systematic and Applied Microbiology* 23:332-336). The strains could be isolated at least twice from the same individual with one to four weeks between the samplings, which strongly indicate that the strains had a certain ability to colonise the GI-tract. The strains were identified by ribotyping, that is Restriction Fragment Length Polymorphism, RFLP, of the 16S rRNA gene, and by REA, that is Restriction Endonuclease Analysis.

The following strains were isolated:
1) *Bifidobacterium infantis* CURE 19; able to grow on Rogosa agar and to ferment oatmeal gruel to some degree, "sour" smell after fermentation.
2) *Bifidobacterium* CURE 20; able to grow on Rogosa agar and to ferment oatmeal gruel to some degree, "sour" smell after fermentation.
3) *Bifidobacterium infantis* CURE 21; able to grow on Rogosa agar and to ferment oatmeal gruel to some degree, "sour" smell after fermentation.
4) *Bifidobacterium* CURE 22; able to grow on Rogosa agar and to ferment oatmeal gruel to some degree, "nice" smell after fermentation.
5) *Bifidobacterium* CURE 23; able to grow on Rogosa agar and to ferment oatmeal gruel to some degree, "nice" smell after fermentation.
6) *Bifidobacterium infantis* CURE 24; able to grow on Rogosa agar and to ferment oatmeal gruel to some degree, "nice" smell after fermentation.
7) *Bifidobacterium* CURE 25; able to grow on Rogosa agar and to ferment oatmeal gruel.
8) *Bifidobacterium infantis* CURE 26; able to grow on Rogosa agar and to ferment oatmeal gruel.
9) *Bifidobacterium dentium* CURE 27; able to grow on Rogosa agar and to ferment oatmeal gruel.
10) *Bifidobacterium infantis* CURE 28; able to grow on Rogosa agar and to ferment oatmeal gruel.
11) *Bifidobacterium infantis* CURE 29; able to grow on Rogosa agar and to ferment oatmeal gruel.
12) *Bifidobacterium infantis* CURE 30; able to grow on Rogosa agar and to ferment oatmeal gruel.

Glutamine Production

The isolated strains 1-12 were tested for production of glutamine in broth by the following procedure.

The test strains were cultured at 37° C. for 4 days in a growth medium (broth) modified from the medium described by Matteuzzi et al. (Ann. Microbil. (Inst. Pasteur, 1978, 129 B: 175-181). The broth was composed of: sodium acetate, 10 g/l; ascorbic acid, 10 g/l; ammonium sulphate ($(NH_4)_2SO_4$), 5 g/l; dipotassium hydrogen phosphate ($K_2HPO_4$), 3 g/l; potassium di-hydrogen phosphate ($KH_2PO_4$), 3 g/l; $MgSO_4 \times 7H_2O$, 0.32 g/l; $FeSO_4 \times 7H_2O$, 0.01 g/l; $MnSO_4H_2O$, 0.007 g/l; NaCl, 0.01 g/l; yeast extract, 0.5 g/l; glucose, 20 g/l; Tween 80, 1 ml/l. pH was adjusted with 1 M NaOH to 6.18-6.24 prior to autoclavation.

The glutamine concentration in the broth was measured before inoculation with bacteria and after growth of the test strain. After growth, the culture was centrifuged and sterile filtered, and the cell-free supernatant subsequently frozen at −80° C. The amino acids were analysed in an automated analyser (Biochrom 20, Pharmacia Biotech) after addition of sulpho-salicylic acid and pH adjustment with lithiumhydroxide.

The increase in the glutamine and glutamic acid concentration in the broth after the growth of different test strains is shown in Table 1 below.

TABLE 1

Increased concentration of glutamine and reduction/production of glutamic acid in the culture broth after growth of the tested *Bifidobacterium* strains.

| Test strain | Glutamine (μmol/l) | Glutamic acid [reduction (R), production (P) in μmol/l] |
|---|---|---|
| *B. infantis* CURE 19 | 53 (29-67)[#] | R |
| *Bifidobacterium* CURE 20 | 4.2 (3.5-4.8)[§] | R |
| *B. infantis* CURE 21 | 37 (36-38)[#] | P 37 (31-41) |

TABLE 1-continued

Increased concentration of glutamine and reduction/production
of glutamic acid in the culture broth after growth
of the tested *Bifidobacterium* strains.

| Test strain | Glutamine (μmol/l) | Glutamic acid [reduction (R), production (P) in μmol/l] |
|---|---|---|
| *Bifidobacterium* CURE 22 | 16 (14-18)§ | R |
| *Bifidobacterium* CURE 23 | 8.9 (8.1-9.6)§ | R |
| *B. infantis* CURE 24 | 3.0 (0-5.9)§ | R |
| *B. infantis* CURE 25 | 35 | R |
| *B. infantis* CURE 26 | 36 | P 60 |
| *B. dentium* CURE 27 | 7.4 | R |
| *B. infantis* CURE 28 | 35 | R |
| *B. infantis* CURE 29 | 28 | R |
| *B. infantis* CURE 30 | 37 | R |

The mean value of three samples derived from three separate cultures
§The mean value of two samples derived from two separate cultures All test strains produced some glutamine but only seven of the 12 tested strains had a relatively high production of glutamine (>20 μmol/l). For all but two strains (CURE 21 and CURE 26), the increase in glutamine occurred along with a strong reduction of glutamic acid in the medium. Medium to which no bacteria were added had an average start concentration of glutamic acid of 223 μmol/l, while the content of glutamine was zero. The three strains CURE 20, CURE 23 and CURE 24 consumed all available glutamic acid in the medium while CURE 28 decreased the concentration of glutamic acid with 247 μmol/l, CURE 29 with 220 μmol/l, CURE 22 with 187 μmol/l, CURE 19 with 128 μmol/l, CURE 30 with 160 μmol/l, CURE 27 with 151 μmol/l, and CURE 25 with 47 μmol/l. It can be speculated if these bacteria convert glutamic acid to glutamine. Two strains, CURE 21 and CURE 26, produced glutamine without any reduction of the glutamic acid concentration in the medium. In contrast to the other strains, they increased the level of glutamic acid in the broth.

Arginine Production

The amino acid production of each test strain was measured after growth of the test strain at 37° C. for 4 days in a growth medium (broth) modified from the medium described by Matteuzzi et al. (1978). The broth was composed of: sodium acetate, 10 g/l; ascorbic acid, 10 g/l; ammonium sulphate ((NH$_4$)$_2$SO$_4$), 5 g/l; dipotassium hydrogen phosphate (K$_2$HPO$_4$), 3 g/l; potassium dihydrogen phosphate (KH$_2$PO$_4$), 3 g/l; MgSO$_4$×7H$_2$O, 0.32 g/l; FeSO$_4$×7H$_2$O, 0.01 g/l; MnSO$_4$H$_2$O, 0.007 g/l; NaCl, 0.01 g/l; yeast extract, 0.5 g/l; glucose, 20 g/l; Tween 80, 1 ml/l. pH was adjusted with 1 M NaOH to 6.18-6.24 prior to autoclavation.

The amino acid concentration in the broth was measured before inoculation with bacteria and after growth of the test strain. After growth, the culture was centrifuged and sterile filtered, and the cell-free supernatant subsequently frozen at −80° C. The amino acids were analysed in an automated analyser (Biochrom 20, Pharmacia Biotech) after addition of sulphosalicylic acid and pH adjustment with lithium-hydroxide.

The increase in the concentration of arginine and citrulline in the broth after the growth of the different test strains is shown in Table 2.

TABLE 2

Increased concentration of arginine and citrulline
in the broth after growth of the test strains.

| Test strain | Arginine (μmol/l) | Citrulline (μmol/l) |
|---|---|---|
| *B. infantis* CURE 19 | 11 (8.8-14)# | 52 (9.2-136)# |
| *Bifidobacterium* CURE 20 | 0§ | 4.1 (4.4-3.7)§ |

TABLE 2-continued

Increased concentration of arginine and citrulline
in the broth after growth of the test strains.

| Test strain | Arginine (μmol/l) | Citrulline (μmol/l) |
|---|---|---|
| *B. infantis* CURE 21 | 0# | 0# |
| *Bifidobacterium* CURE 22 | 0§ | 6.3 (5.8-6.7)§ |
| *Bifidobacterium* CURE 23 | 2.0 (0-3.9)§ | 6.1 (5.4-6.8) |
| *B. infantis* CURE 24 | 0§ | 0§ |
| *B. infantis* CURE 25 | 0 | 4.2 |
| *B. infantis* CURE 26 | 2.6 | 0 |
| *B. dentium* CURE 27 | 4.9 | 0.0 |
| *B. infantis* CURE 28 | 37 | 202 |
| *B. infantis* CURE 29 | 26 | 13 |
| *B. infantis* CURE 30 | 2.0 | 5.7 |

The mean value of three samples derived from three separate cultures
§The mean value of two samples derived from two separate cultures Three of the 12 test strains increased the concentration of arginine with more than 10 μmol/l, that is 0.5 CURE 19 CURE 28 and CURE 29. Two of said strains also had a strikingly strong production of citrulline (>100 μmol/l), that is CURE 19 and CURE 28. Citrulline is produced either by deamination of arginine or through NO-synthase and generation of NO. The citrulline production also reflects arginine production in an earlier step.

Also other amino acids penetrated out into the broth during growth of the test strains, see Table 3. CURE 21 did not produce any citrulline or arginine but significant amounts of asparagine acid and tyrosine. CURE 26 did not produce any citrulline but very small amounts of arginine and a wide spectrum of different amino acids. Furthermore, CURE 26 was the only test strain that increased the concentration of proline in the broth. All test strains produced threonine.

TABLE 3

Increase in amino acid concentrations (μmol/l), in
addition to glutamine, glutamic acid, arginin, and citrullin
in the broth after growth of the test strains.

| Strain | Thr | Tyr | Cys | Asp | Ala | Gly | Ile |
|---|---|---|---|---|---|---|---|
| CURE 19 | 39 | 15 | 0 | 23 | 15 | 0 | 0 |
| CURE 21 | 51 | 21 | 0 | 96 | 0 | 0 | 0 |
| CURE 26 | 46 | 46 | 12 | 151 | 61 | 0 | 6 |
| CURE 28 | 44 | 12 | 14 | 0 | 0 | 0 | 0 |
| CURE 29 | 35 | 28 | 0 | 0 | 2 | 0 | 0 |

Thr—threonine;
Tyr—tyrosine;
Cys—cysteine;
Asp—asparagine acid;
Ala—alanine;
Gly—glycine;
Ile—isoleucine The values represent mean values of three or two samples derived from three or two separate cultures.

Genotypic Identification

REA

The strains were examined as to the cleavage pattern of the chromosomal DNA, through restriction-endonuclease analysis—REA—method according to Ståahl M, Molin G, Persson A, Ahrné S & Ståhl S, International Journal of Systematic Bacteriology, 40:189-193, 1990, and further developed by Johansson, M-L, et al., International Journal of Systematic Bacteriology 45:670-675, 1995. Schematically REA can be described as follows: Chromosomal DNA from the strains involved in the study were prepared and cleaved by restriction endonucleases. 0.75 μg of each DNA was separately digested at 37° C. for 4 h with 10 units of EcoRI and Hind III; each endonuclease was used separately. The cleaved DNA fragments are separated as to size by gel electrophoresis using submerged horizontal agarose slab gels. The gels consisted of 150 ml of 0.9% agarose (ultrapure DNA grade; low electro-endo osmosis; BioRad Laboratories, Richmond, USA) and were cast as slab gels (150 by 235 mm). 0.2 µg of the High Molecular Weight DNA marker (Bethesda Research Laboratories, MD, USA) together with 0.5 µg of a DNA molecular weight marker VI (Roche, Germany) were used as standards. Minimal band distortion and maximal sharpness were achieved by applying the sample DNA in Ficoll loading buffer (2 g of Ficoll, 8 ml of water, 0.25% bromphenol).

Gels were run at a constant voltage of 40V for 18 h at about 6-8° C. The buffer (89 mM Tris, 23 mM $H_3PO_4$, 2 mM sodium EDTA, pH 8.3) was recirculated during the running period. Thereafter, the gels were stained for 20 minutes in ethidium bromide (2 µg/ml) and destained in distilled water, visualized at 302 nm with a UV transilluminator (UVP Inc., San Gabriel, USA) and photographed. This way of running the gel electrophoresis gave well distributed and relatively well-separated band down to a molecular weight of $1.2 \times 10^6$.

RFLP of the 16S rRNA Gene (Ribotyping)

Preparation of chromosomal and Restriction Endonuclease Analysis of chromosomal DNA was performed as described earlier (Ståhl et al., 1990, Ståhl et al., 1994).

The probe was a 420 bp fragment (position 506 to 926, *E. coli* numbering) of the 16S rRNA gene of *L. casei* ssp. *pseudoplantarum* DSM 20008, obtained by PCR and labelled by DIG DNA labelling technique according to the instructions supplied by the manufacturer (Boehringer Mannheim, Bromma, Sweden). The amount of probe used in the reactions was 50 ng.

Southern blot hybridisation. One µg of the chromosomal DNA was digested with 10U of EcoRI and HindIII (Boehringer Mannheim) for 4 h at 37° C. Separation of restriction fragments by agarose gel electrophoresis was performed according to Ståhl et al., 1994. DIG-labelled Molecular weight DNA marker II and Molecular weight DNA marker VI were used as standards (Roche, Germany). The DNA was immobilised on a positively charged nylon membrane (Roche) by baking for 30 min at 120° C. Prehybridisation, hybridisation and chemoluminescent detection with the substrate CSPD® (Roche) were performed according to the instructions supplied by the manufacturer. The hybridisation temperature was 68° C. The test resulted in one single band with a molecular weight of about 2840 kb in for all strains (CURE 19, 21, 26, 28 and 29) when chromosomal DNA was cleaved by Hind III. When chromosomal DNA was cleaved by EcoRI, the genes for 16S rRNA ended up on a single fragment with the molecular weight of about 895 kb in strains CURE 21 and 26, while another single band with a molecular weight of about 3420 kb was obtained for strains CURE 19, 28 and 29.

Test In Vivo

Test 1. Effects of *Lactobacillus* and *Bifidobacterium* Strains on DDS Induced Colitis in Rat The aim of this study was to compare the effects of *Lactobacillus* and *Bifidobacterium* strains on DDS (Dextran Sodium Sulfate) induced colitis in rat.

Sprague Dawley rats were divided into six groups, one control group (colitis without administration of bacteria), and five groups to which different bacterial strains (*Lactobacillus plantarum* 299v, *Lactobacillus paracasei* 8700:2, *Lactobacillus gasseri* LG1, Bifidobacterium 3B1 and *Bifidobacterium infantis* CURE 19, respectively) were administered. The bacterial strains were administered orally for 7 days prior to the induction of colitis (day 0) and were continuously administered for 7 days in combination with DDS (5% w/v dissolved in water). The degree of colitis were determined daily with DAI (Disease Activity Index). Sampling was performed day 14 and bacterial translocation and quantity in the intestine determined.

In the groups receiving *Lactobacillus plantarum* 299v, Bifidobacterium 3B1 and *Bifidobacterium* CURE 19, DAI decreased significantly day 4, 5, 6 and 7 compared to the control group. In addition, DAI was significantly lower in the group receiving *B. infantis* CURE 19 compared to the groups receiving *Lactobacillus paracasei* 8700:2 and *Lactobacillus gasseri* LG1 after 6 and 7 days. Compared to the control colitis, the bacterial translocation to the mesenteric lymph nodes decreased significantly in all groups as well as the translocation of Enterobacteriaceae to the liver.

Figure 1:
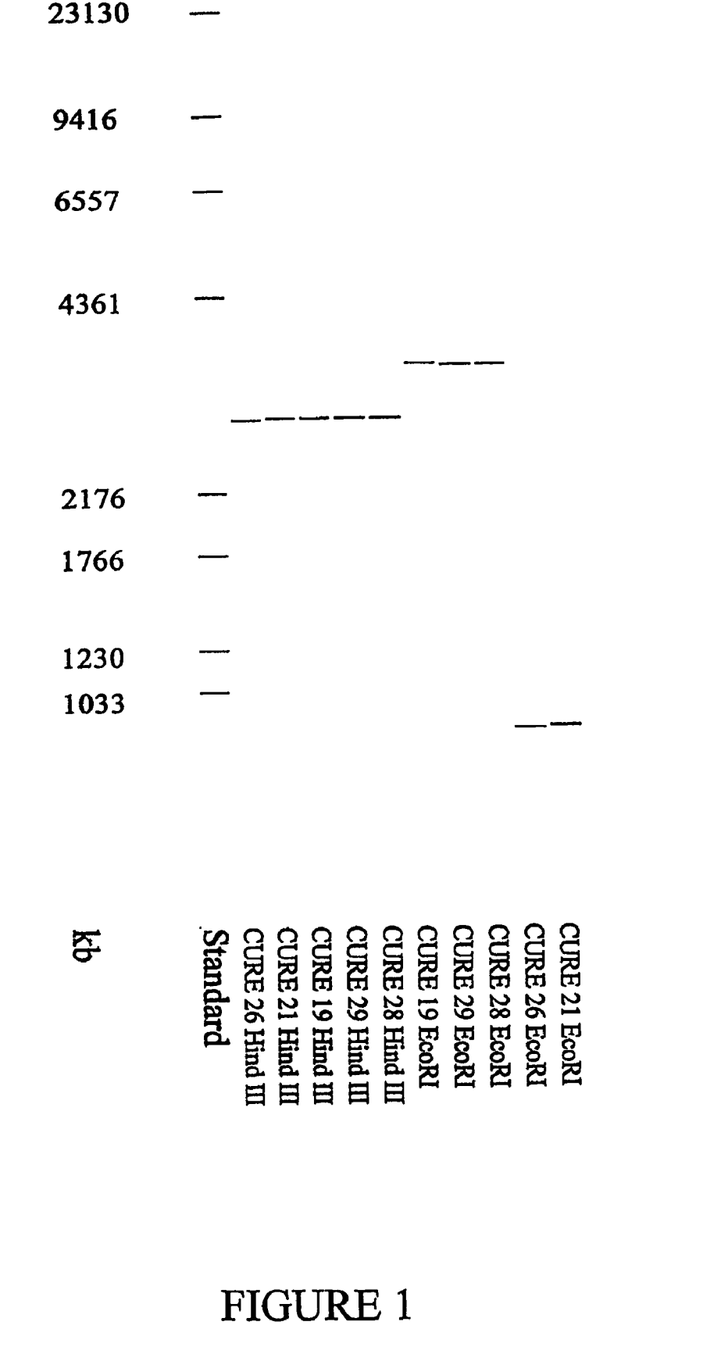
FIG. 1 is a schematic representation of the electrophoretic patterns obtained with Restriction Fragment Length Polymorphism (RFLP) for the strains CURE 19, CURE 21, CURE 26, CURE 28, and CURE 29, obtained by cleaving chromosomal DNA with EcoRI and Hind III, respectively, followed by hybridisation with a DIG-labelled 420 bp fragment probe (position 506 to 926, *E. coli* numbering) of the 16S rRNA gene of *L. casei* subsp. *pseudoplantarum* DSM 20008 using Southern blot hybridisation. Dig-labelled Molecular weight DNA marker II (Roche) and Molecular weight DNA marker VI (Roche) were used as standard.
Figure 2:
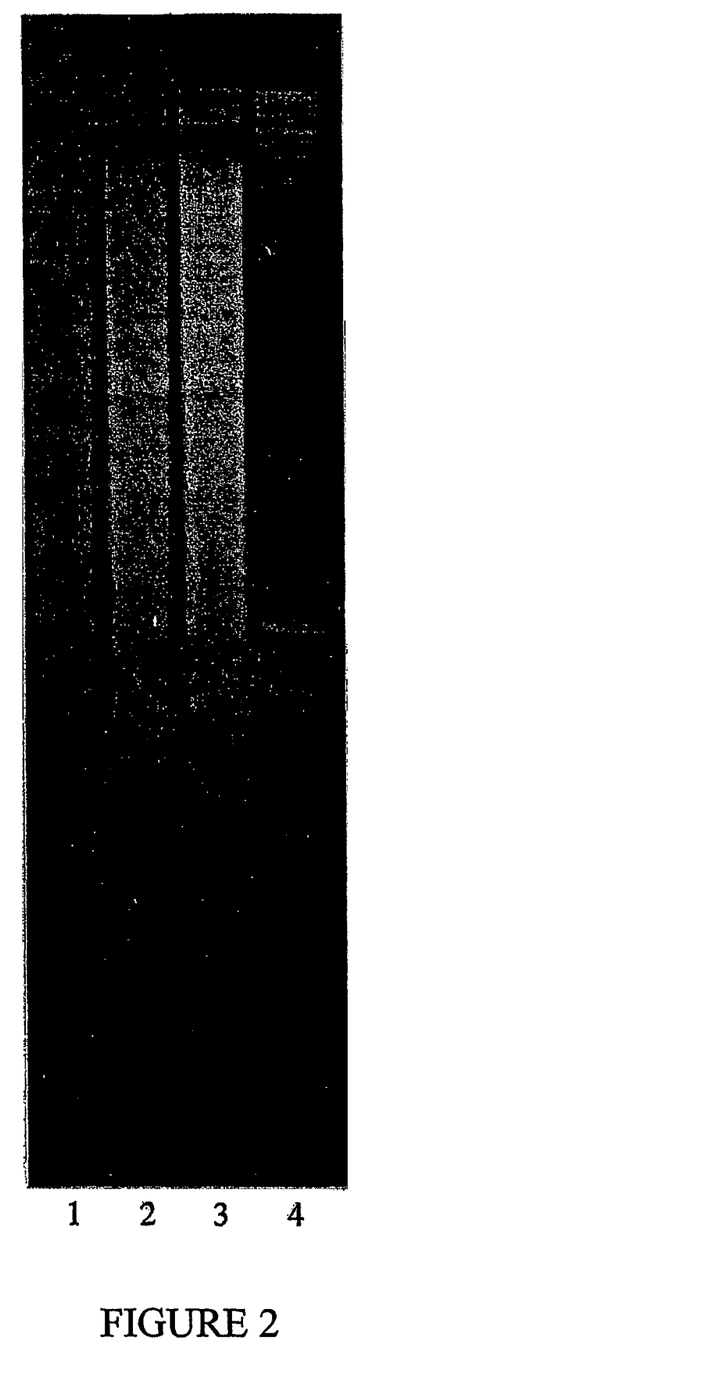
FIG. 2 shows a photograph of separated DNA fragments obtained by cleaving chromosomal DNA of strains CURE 19 (lane 1), CURE 29 (lane 2) and CURE 28 (lane 3) with the restriction enzyme EcoRI (Restriction Endonuclease Analysis, REA). High Molecular Weight DNA marker (BRL) and DNA molecular weight marker VI (Roche) were used as standard (lane 4).
Figure 3:
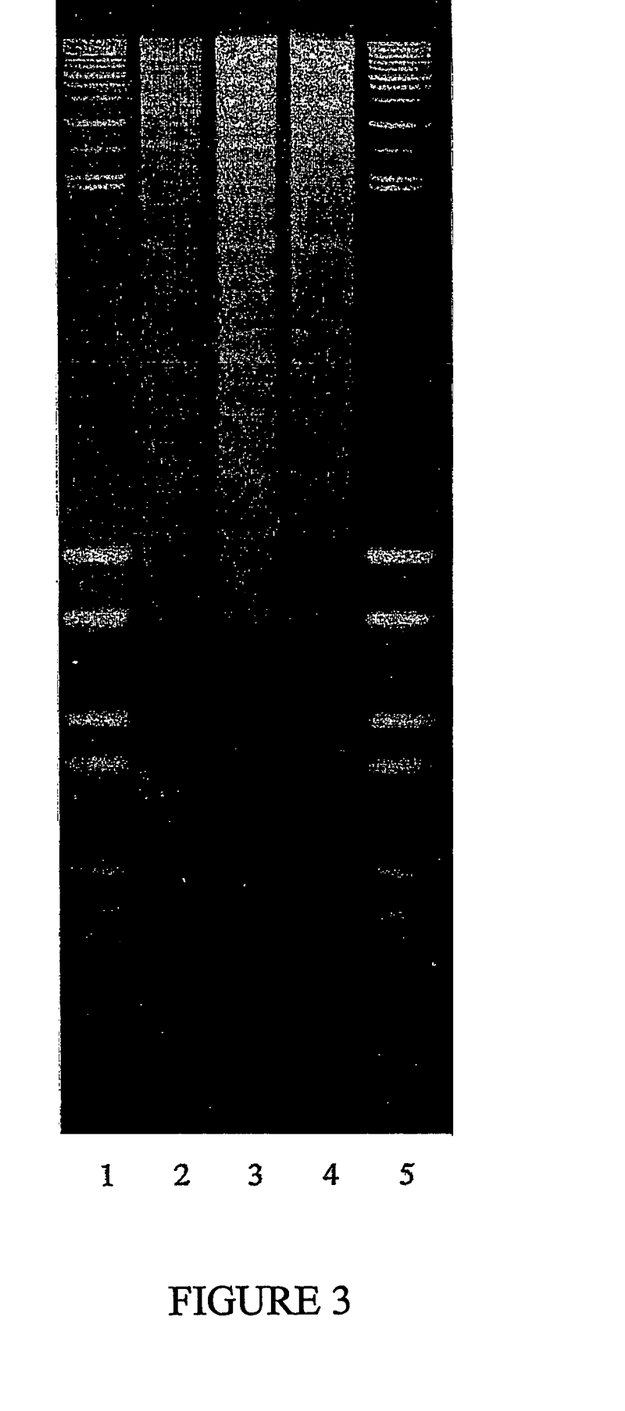
FIG. 3 shows a photograph of separated DNA fragments obtained by cleaving chromosomal DNA of strains CURE 19 (lane 2), CURE 28 (lane 3) and CURE 29 (lane 4) with the restriction enzyme Hind III. High Molecular Weight DNA marker (BRL) and DNA molecular weight marker VI (Roche) were used as standards (lanes 1 and 5).
Figure 4:
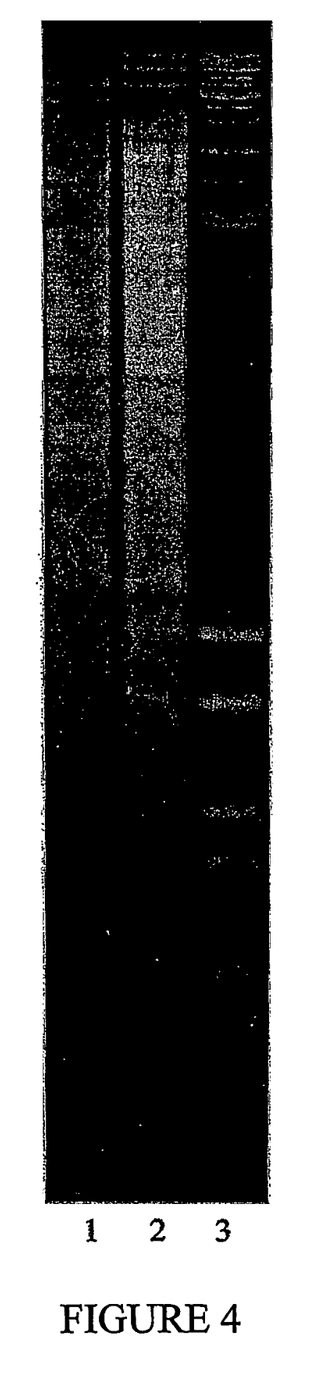
FIG. 4 shows a photograph of separated DNA fragments obtained by cleaving chromosomal DNA of strains CURE 21 (lane 1) and CURE 26 (lane 2) with the restriction enzyme EcoRI. High Molecular Weight DNA marker (MD, USA) and DNA molecular weight marker VI (Roche) were used as standard (lane 3).
Figure 5:
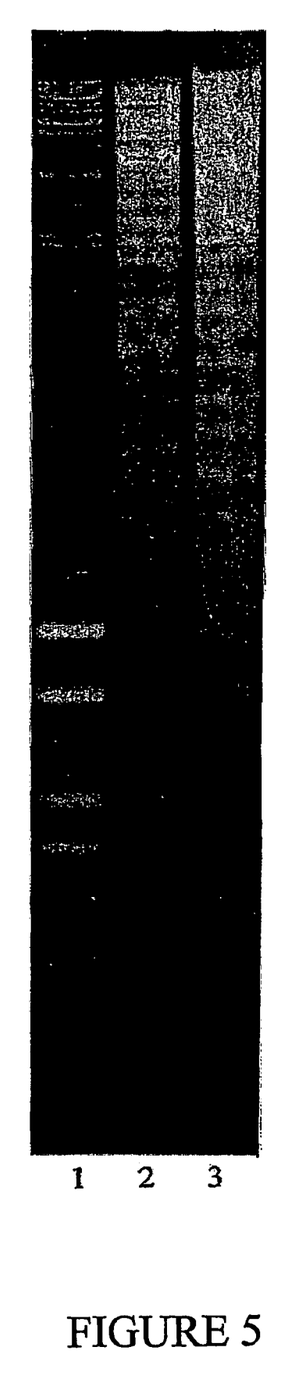
FIG. 5 shows a photograph of separated DNA fragments obtained by cleaving chromosomal DNA of strains CURE 21 (lane 2) and CURE 26 (lane 3) with the restriction enzyme Hind III. High Molecular Weight DNA marker (MD, USA) and DNA molecular weight marker VI (Roche) were used as standards (lanes 1 and 4).
Figure 6:
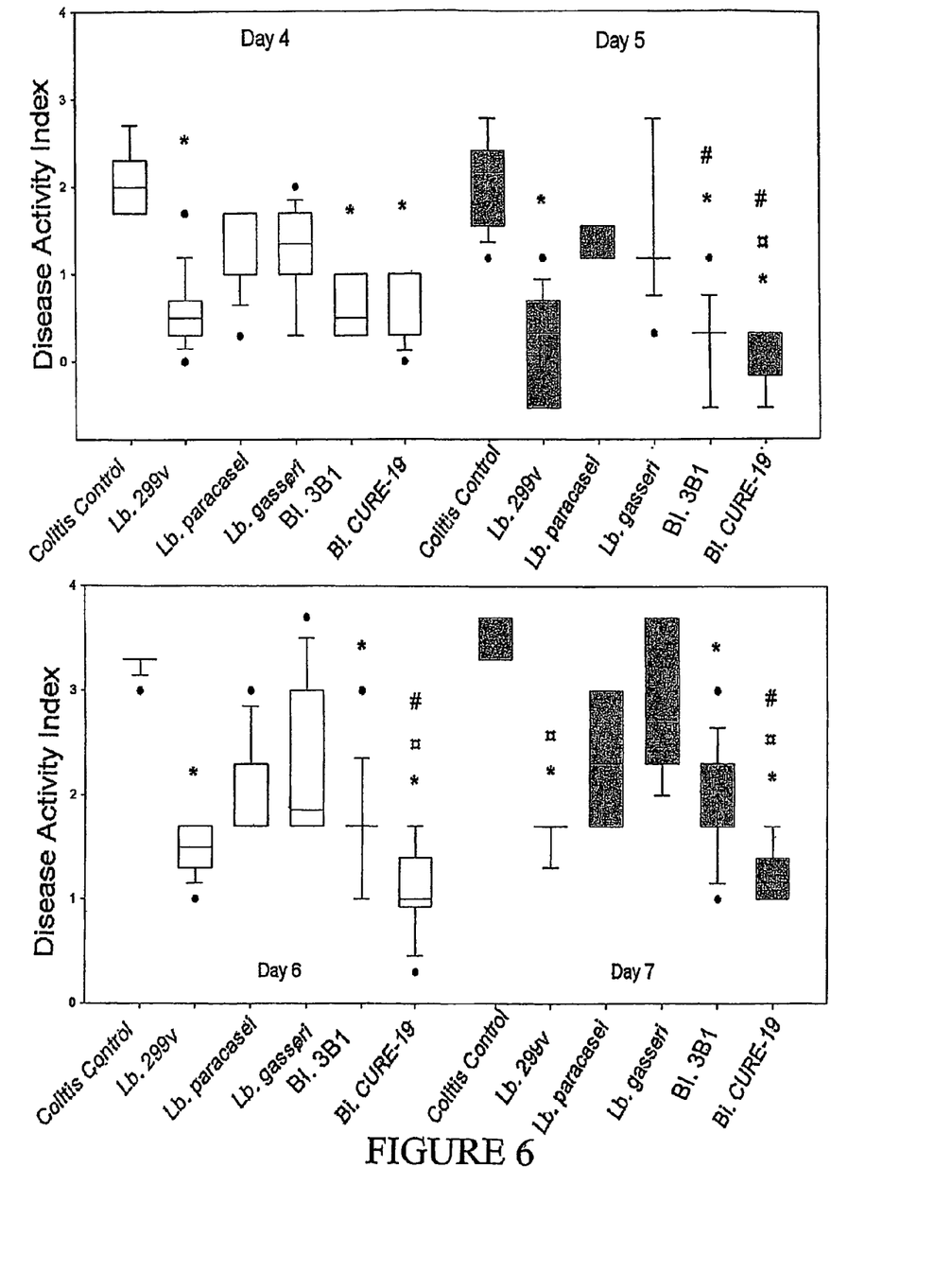
FIG. 6. Disease activity index on day 4, 5, 6 and 7. * denotes p<0.05 compared to colitis control, □ denotes p<0.05 compared to *L. gasseri*, # denotes p<0.05 compared to *L. paracasie*.

In conclusion, oral administered bacterial strains of *Lactobacillus plantarum* 299v, *Lactobacillus paracasei* 8700:2, *Lactobacillus gasseri* LG1, Bifidobacterium 3B1 and *Bifidobacterium infantis* CURE 19 are able to exercise positive effects by decreasing translocation on experimental colitis in rats. *Lactobacillus plantarum* 299v, Bifidobacterium 3B1 and *Bifidobacterium infantis* CURE 19 showed the most evident effects in improved DAI in the DDS induced colitis rat. *Bifidobacterium infantis* CURE 19 was somewhat more effective in counteracting the colitis than the others after 6d and 7d of treatment. Please see FIG. 6.

Test 2. Survival of *Lactobacillus* and/or *Bifidobacterium* in the GI-Tract After Oral Administration Oral administration of *Lactobacillus* or *Bifidobacterium* provides different positive effects, e.g. preventing antibiotic associated diarrhoea (D'Souza et al., 2002, BMJ 324:1361)

Positive effects may be achieved provided that the bacteria survive the oral administration and have the ability to survive and thrive in the intestines. To find suitable strains that can be used as probiotics, a number of possible candidate strains are administered orally to healthy subjects. Determination of the frequency of the administered strains in the faeces identifies strains with high survival ability. The aim of this study is to find orally administrable bacterial strains with a superior ability to survive and thrive in the human GI-tract.

Design of the Study

For four weeks fourteen voluntary subjects are to drink a mixture of approximately 20 different strains of *Lactobacillus* and *Bifidobacterium*. All strains are representatives of strains occurring in humans or in lactic acid producing food. Faecal sampling will be taken before administration, after 3 weeks of administration and one week post administration. The bacterial flora is determined by viable count and RAPD (Randomly Amplified Polymorphic DNA; Johansson et al., 1995).

CONCLUSION

The results show that the selected strains, that is *Bifidobacterium infantis* CURE 19, DSM 15158; Bifidobacterium CURE 21, DSM 15159; *Bifidobacterium infantis* CURE 26, DSM 15160; *Bifidobacterium infantis* CURE 28, DSM 15161; and *Bifidobacterium infantis* CURE 29, DSM 15162, can survive the passage through the gastrointestinal tract after oral administration. Studies in rats also show a potential of exercising positive effects on experimental colitis.

The invention claimed is:

1. A biologically pure culture of a strain of *Bifidobacterium infantis* selected from the group consisting of *Bifidobacterium infantis* CURE 19, DSM 15158, *Bifidobacterium infantis* CURE 21, DSM 15159, *Bifidobacterium infantis* CURE 26, DSM 15160, *Bifidobacterium infantis* CURE 28, DSM 15161, and *Bifidobacterium infantis* CURE 29, DSM 15162, wherein said strain survives in the intestinal tract of a human being and produces glutamine in vivo.

2. The biologically pure culture of a strain of *Bifidobacterium infantis* according to claim 1, wherein said strain is selected from the group consisting of *Bifidobacterium infantis* CURE 19, DSM 15158, *Bifidobacterium infantis* CURE 28, DSM 15161, and *Bifidobacterium infantis* CURE 29, DSM 15162, and wherein said strain survives in the intestinal tract of a human being and produces glutamine and arginine in vivo.

3. The biologically pure culture of a strain of *Bifidobacterium infantis* according to claim 1, wherein said strain assimilates ammonia.

* * * * *